US008450353B2

(12) United States Patent
Ptchelintsev et al.

(10) Patent No.: US 8,450,353 B2
(45) Date of Patent: May 28, 2013

(54) TOPICAL COMPOSITIONS CONTAINING DESTHIOBIOTIN AND ITS DERIVATIVES AND A METHOD OF TREATING SKIN

(75) Inventors: Dmitri S. Ptchelintsev, Jersey City, NJ (US); Xiaochun Luo, New City, NY (US); Siming W. Chen, Parsippany, NJ (US)

(73) Assignee: Avon Products, Inc., New York, NY (US)

( * ) Notice: Subject to any disclaimer, the term of this patent is extended or adjusted under 35 U.S.C. 154(b) by 145 days.

(21) Appl. No.: 12/747,364

(22) PCT Filed: Nov. 19, 2008

(86) PCT No.: PCT/US2008/084005
§ 371 (c)(1),
(2), (4) Date: Jun. 10, 2010

(87) PCT Pub. No.: WO2009/085443
PCT Pub. Date: Jul. 9, 2009

(65) Prior Publication Data
US 2010/0267792 A1    Oct. 21, 2010

Related U.S. Application Data

(60) Provisional application No. 61/015,703, filed on Dec. 21, 2007.

(51) Int. Cl.
| | | |
|---|---|---|
| A61K 31/12 | (2006.01) | |
| A01N 43/50 | (2006.01) | |
| C07C 59/86 | (2006.01) | |
| C07D 413/00 | (2006.01) | |

(52) U.S. Cl.
USPC ............ 514/396; 514/676; 562/459; 544/132

(58) Field of Classification Search
None
See application file for complete search history.

(56) References Cited

U.S. PATENT DOCUMENTS

| | | |
|---|---|---|
| 4,243,665 A | 1/1981 | Purcell et al. |
| 4,529,587 A * | 7/1985 | Green ......................... 424/70.8 |
| 5,492,894 A | 2/1996 | Bascom et al. |
| 7,255,857 B2 | 8/2007 | Li et al. |
| 2005/0188427 A1 | 8/2005 | Li et al. |

FOREIGN PATENT DOCUMENTS

GB            2252940 A        8/1992

OTHER PUBLICATIONS

Gail Jenkins, Molecular mechanisms of skin ageing, 123 (2002) 801-810.*
Weiss et al., Topical Treninoin Improves Photoaged Skin, A Double-blind Vehicle-Controlled Study, JAMA, Jan. 22-29, 1988, vol. 259, No. 4, pp. 527-532 ("JAMA 1").*
Gilchrest, At Last! A Medical Treatment for Skin Aging, JAMA, Jan. 22-29, 1988, vol. 259, No. 4, pp. 569-570 ("JAMA 2").*
Liu et al.; Elastic fiber homeostasis requires lysyl oxidase-like 1 protein; Nat Genet. 36(2):178-82, 2004.
Noblesse E. et al.; Lysyl Oxidase-Like and Lysyl Oxidase Are Present in the Dermis and Epidermis of a Skin Equivalent and in Human Skin and Are Associated to Elastic Fibers; J Invest Dermatol. 122(3):621-30) (2004).
Pascual et al.; Down-regulation of lysyl oxydase-like in aging and venous insufficiency; Histol Histopathol. 23 (2):179-86) (2008).
Leonian and Lilly (1945) Conversion of Desthiobiotin Into Biotin or Biotinlike Substances by Some Microorganisms. J Bacteriol. 49(3): 291-297.
Kagan et al.; Lysyl Oxidase: Properties, Specificity, and Biological Roles Inside and Outside of the Cell; J. Cell. Biochem. 88:660-672, 2003.
Kielty et al.; Fibrous Proteins: Coiled-Coils Collagen and Elastomers, Adv. in Protein Chemistry, vol. 70, p. 405, 2004.
du Vingneaud et al.; "The Structure of Biotin: A Study of Desthiobiotin"; The Journal of Biological Chemistry 146 (2):475, Dec. 1, 1942, structure IV.

* cited by examiner

*Primary Examiner* — Sreeni Padmanabhan
*Assistant Examiner* — Svetlana M Ivanova
(74) *Attorney, Agent, or Firm* — Charles J. Zeller; David M. Royal; Joan M. McGillycuddy

(57) ABSTRACT

Topical compositions and methods of use to treat symptoms of reduced skin elasticity are provided comprising desthiobiotin and certain desthiobiotin analogues. These compounds are effective in stimulating LOXL-1 activity and can thus increase elastin remodeling and improve appearance of fine lines, wrinkles, skin sagging and other symptoms of reduced elastin function.

27 Claims, No Drawings

TOPICAL COMPOSITIONS CONTAINING DESTHIOBIOTIN AND ITS DERIVATIVES AND A METHOD OF TREATING SKIN

RELATED APPLICATIONS

This application claims priority to International Application Serial No. PCT/US08/84005 filed Nov. 19, 2008, which claims priority U.S. Provisional Patent Application Ser. No. 61/015,703, filed Dec. 21, 2007, the contents of which are hereby incorporated by reference in their entirety.

FIELD OF INVENTION

The present invention relates to topical compositions containing desthiobiotin, as well as derivatives and isomers thereof, and methods of use of such compositions for treating, reversing, and/or preventing signs of skin aging, including fine lines and wrinkles in the skin.

BACKGROUND OF THE INVENTION

The gradual development of facial wrinkles, whether fine surface lines or deeper creases and folds, is the classic early sign of accumulated skin damage and aging. Premature aging and wrinkling of the skin may be accelerated by excessive exposure to the sun and other elements, overactive facial expression muscles, the frequent use of tobacco products, poor nutrition, or skin disorders. Fine surface wrinkles that progress to deeper creases, deepening facial expression due to repeated skin folding, and deep folds which develop with one's maturity are obvious changes which may combine to portray a less desirable appearance. Several invasive techniques are available in which substances are injected or implanted in the area of the skin which either temporarily weaken the muscles or act as skin volume fillers, however non-invasive treatments have historically met with only minimal success. Regardless of the cause of facial creases or folds, safe and effective treatments for reduction or elimination of these problems has been exceedingly difficult to achieve.

Skin elasticity is critical for improving damage such as sagging, reduced skin firmness and youthful appearance, and improving the appearance of fine lines and wrinkles. All these are made possible by elastin, a protein polymer that works like a rubber band, repeatedly stretching and contracting without suffering any damage.

Elastin polymers are formed by the cross-linking of tropoelastin monomers. Although there are as many as five enzymes that can catalyze this process, it is unclear exactly how the crosslinking is regulated. Li and colleagues have reported that one of these enzymes, lysyl oxidase-like 1 (LOXL1) is essential for remodeling elastin fibers. Liu and colleagues predicted that the enzyme is recruited to sites of elastin by the extracellular-matrix protein fibulin-5. LOXL1 then primes tropoelastin monomers (TE) for incorporation into the larger polymer. Liu found that LOXL1 is necessary to prevent age-related loss of elasticity in tissues such as arteries and lungs (Liu, et al. (2004) Elastic fiber homeostasis requires lysyl oxidase-like 1 protein. *Nat Genet.* 36(2):178-82).

Noblesse, et al. have shown that LOXL1 is present in the dermis and the epidermis of both normal skin and in a skin equivalent model (SE). The ultrastructural localization of LOXL was indicative of its association with elastin-positive materials. The investigators hypothesized that LOXL could have a role in elastic fiber formation (Noblesse E, et al. (2004) Lysyl oxidase-like and lysyl oxidase are present in the dermis and epidermis of a skin equivalent and in human skin and are associated to elastic fibers. *J Invest Dermatol.* 122(3):621-30).

Pascual and colleagues have shown levels of markers of elastin synthesis including LOXL1 diminish to a significant extent with age (Pascual, et al. (2008) Down-regulation of lysyl oxydase-like in aging and venous insufficiency. *Histol Histopathol.* 23(2): 179-86).

U.S. Patent Pub. No. 2005/0188427 by Li and Liu discloses a method of treating a subject having a condition associated with a loss of elastic fibers, such as loose or wrinkly skin, comprising administering to the subject a therapeutically effective amount of a LOXL1 enhancer. The LOXL1 enhancers are said to be LOXL1 polypeptides or active fragments thereof, or a nucleic acid encoding a LOXL1 polypeptide or active fragment thereof. The LOXL1 enhancers are also said to include small molecules or other therapeutic compounds identified by the screening method disclosed in that publication.

Desthiobiotin has been known since the mid-1940's as a precursor of biotin in bacteria and molds (see Leonian and Lilly (1945) Conversion of Desthiobiotin Into Biotin or Biotinlike Substances by Some Microorganisms. *J Bacteriol.* 49(3): 291-297). Desthiobiotin is derived from biotin by the removal of the sulfur atom. It can substitute for biotin in some microorganisms, but is without effect on or is inhibitory to the growth of others. The compound has the following structure:

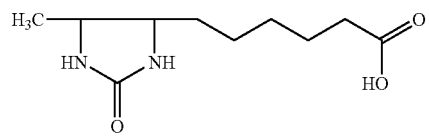

U.S. Pat. No. 4,243,665 describes the use of low concentrations of certain biotin derivatives in tooth care. This patent is based on the idea that compounds such as desthiobiotin can biotin-deplete microorganisms that cause dental decay.

U.S. Pat. No. 4,529,587 to Lever Brothers Corp. describes the use of certain biotin antagonists for decreasing sebum synthesis. These compounds have the general structure:

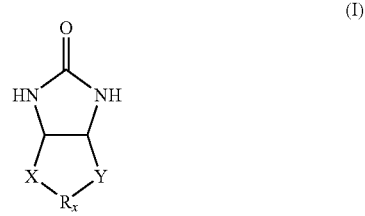

and are described as blocking biotin dependent enzymes that are implicated in lipid synthesis, in particular in their effect against acetyl-SCoA-carboxylase. The compositions are said to be useful for reducing superficial "grease" without defatting the skin.

There remains a need for cosmetic compositions which reduce signs of aging including sagging, reduced elasticity, fine lines and wrinkles, particularly on the skin of the face, neck, hands, etc.

It is therefore an object of the present invention to provide improved compositions and methods of use to improve the appearance of skin, including by reducing the appearance of fine lines and wrinkles.

SUMMARY OF THE INVENTION

It has surprisingly been found that desthiobiotin is efficacious in reducing, reversing, ameliorating, and/or preventing signs of skin aging caused by decreased skin elasticity, including appearance, depth, or severity of fine lines and/or wrinkles, skin sagging and related signs of aging in skin.

Generally, the compositions and methods are useful for treating any skin condition associate with loss of elastic fibers. These benefits are believed to arise, at least in part, from the ability of the compounds to stimulate production of LOXL-1. In other words, the compounds of the invention are LOXL-1 enhancers.

In one aspect of the invention, a method is provided for treating a skin condition associated with reduced skin elasticity, such as the appearance of fine lines, wrinkles and sagging skin, comprising topically applying to skin in need thereof a cosmetic composition comprising an effective amount of a compound of Formula I:

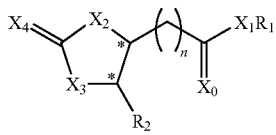

wherein:

n is an integer from 1 to 22, typically from 1 to 3 to 18, and preferably from 5 to 12;

$X_0$, $X_1$, $X_2$, $X_3$ and $X_4$ are each independently selected from the group consisting of O, S, and $NR^N$, where $R^N$ represents hydrogen, lower alkyl (e.g., methyl, ethyl, propyl, butyl, etc.), $COR_3$, $CO_2R_3$, $SO_2R_3$, $PO_3(R_3)_2$, and $CH(OR_3)_2$; where $R^3$ is independently at each occurrence selected from the group consisting of H, alkyl, alkenyl, alkynyl, aryl, heteroaryl, and combinations thereof; $X_2$ and $X_3$ preferably being $NR^N$, and more preferably NH; and $X_0$, $X_1$, and $X_4$ preferably being O;

$R_1$ is selected from the group consisting of H, alkyl, cycloalkyl, alkenyl, alkynyl, aryl, heteroaryl, alkylaryl (e.g., benzyl), alkoxyalkyl, and carboxyamidoalkyl, and combinations thereof;

$R_2$ is selected from the group consisting of H, alkyl, alkenyl, alkynyl, aryl, alkylaryl, heteroaryl, alkoxy, aryloxy, thioalkoxy, and combinations thereof;

and topically acceptable salts thereof and prodrugs thereof.

The compounds of formula I preferably are capable of increasing LOXL1 activity ("LOXL1 enhancers"), and, in certain embodiments, are further capable of stimulation of Fibrillin-1.

In a related aspect of the invention, a method is provided for treating a skin condition associated with reduced skin elasticity, such as the appearance of fine lines or wrinkles, skin sagging or atrophy, enlarged pores, loss of skin resilience or turgor, or loss of skin coloration or tone, comprising topically applying to skin in need thereof an effective amount of a composition comprising a compound having the following structure (or a topically acceptable salt or ester thereof):

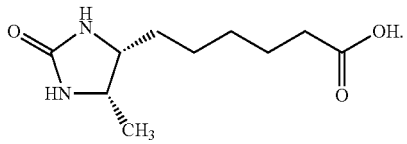

These and other aspects of the invention will be better understood by reference to the following detailed description of the invention.

DETAILED DESCRIPTION

It has surprisingly been found that desthiobiotin is capable of stimulating the production of or enhancing the activity of the LOXL1 enzyme. LOXL1 is an essential enzyme necessary for the maintenance and remodeling of elastin in skin. In view of this finding and others, desthiobiotin and certain derivatives thereof, are contemplated to be useful in combating signs of skin aging, including reducing fine lines and wrinkles, sagging, and related signs of aging in skin.

As used herein, "% by weight" or "% wt" refers to the weight percent of a component in relation to the total weight of the composition (i.e., including any carriers, vehicles, solvents, emollients, fillers, or other components added before application to the skin) unless otherwise specified.

Whenever a term is identified by reference to a range, the range will be understood to explicitly disclose every element thereof. As a non-limiting example, $C_{1-4}$ alkyl will be understood to refer to and disclose $C_1$, $C_2$, $C_3$ or $C_4$ alkyl.

Where two or more substituents are referred to as being "independently selected from" a group of enumerated alternatives, it is meant that each substituent can be any element of that group, independent of the identity of the other substituents.

The present invention provides compositions for topical application which comprise an effective amount of a LOXL1 enhancer, such as desthiobiotin and its structurally related compounds or salts thereof, to treat, reverse, ameliorate and/ or prevent signs of skin aging. Such signs of skin aging include without limitation, the following:

(a) treatment, reduction, and/or prevention of fine lines or wrinkles, (b) reduction of skin pore size, (c) improvement in skin thickness, plumpness, and/or tautness;

(d) improvement in skin suppleness and/or softness;

(e) improvement in skin tone, radiance, and/or clarity;

(f) improvement in procollagen and/or collagen production;

(g) improvement in maintenance and remodeling of elastin;

(h) improvement in skin texture and/or promotion of retexturization;

(i) improvement in skin barrier repair and/or function;

(j) improvement in appearance of skin contours;

(k) restoration of skin luster and/or brightness;

(l) replenishment of essential nutrients and/or constituents in the skin;

(m) decreased by aging and/or menopause;

(n) improvement in skin moisturization; and/or (o) increase in skin elasticity and/or resiliency.

In practice, the compositions of the invention are applied to skin in need of treatment. That is, skin which suffers from a deficiency or loss in any of the foregoing attributes or which would otherwise benefit from improvement in any of the foregoing skin attributes.

In certain preferred embodiments the compositions and methods of the invention are directed to the prevention, treatment, and/or amelioration of fine lines and/or wrinkles in the skin. In this case, the compositions are applied to skin in need of treatment, by which is meant skin having wrinkles and/or fine lines. Preferably, the compositions are applied directly to the fine lines and/or wrinkles. The compositions and methods are suitable for treating fine lines and/or wrinkles on any surface of the skin, including without limitation, the skin of the face, neck, and/or hands.

The LOXL1 enhancing compounds typically have the structure of Formula I:

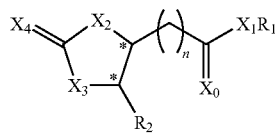

I wherein:

n is an integer from 1 to 22, typically from 1 to 3 to 18, and preferably from 5 to 12;

$X_0$, $X_1$, $X_2$, $X_3$ and $X_4$ are each independently selected from the group consisting of O, S, and $NR^N$, where $R^N$ represents hydrogen, lower alkyl (e.g., methyl, ethyl, propyl, butyl, etc.), $COR_3$, $CO_2R_3$, $SO_2R_3$, $PO_3(R_3)_2$, and $CH(OR_3)_2$; wherein $R_3$ is selected from the group consisting of H, alkyl, alkenyl, alkynyl, aryl, heteroaryl, and combinations thereof; $X_2$ and $X_3$ preferably being $NR^N$, and more preferably NH; and $X_0$, $X_1$, and $X_4$ preferably being O;

$R_1$ is selected from the group consisting of H, alkyl, cycloalkyl, alkenyl, alkynyl, aryl, heteroaryl, alkylaryl (e.g., benzyl), alkoxyalkyl, carboxyamidoalkyl, and combinations thereof; and in the case where $X_0$ and $X_1$ are both O, $R_1$ is preferably H (to thereby define a carboxylic acid) or alkyl (to thereby define an ester);

$R_2$ is selected from the group consisting of H, alkyl, alkenyl, alkynyl, aryl, alkylaryl, heteroaryl, alkoxy, aryloxy, thioalkoxy, and combinations thereof; preferably $R_2$ is H or lower alkyl such as methyl, ethyl, propyl, and the like;

and topically acceptable salts and prodrugs thereof;

The term "alkyl" is used herein, unless otherwise specified, includes straight, branched, or cyclic (also identified as cycloalkyl), primary, secondary, or tertiary hydrocarbons, including but not limited to those of $C_1$ to $C_{18}$, and more specifically $C_{1-6}$. Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more heteroatoms or moieties selected from the group consisting of halo, hydroxyl, carboxyl, acyl, acyloxy, amino, alkylamino, dialkylamino, arylamino, amido, esters, carbamide, alkoxy, aryloxy, nitro, cyano, oxo, oxa, thio, sulfonyl, ester, amide, phosphonyl, phosphinyl, thioether, oxime, or any other functional group that does not inhibit the pharmacological activity of this compound. Preferred substitutions include halogen (fluoro, chloro, bromo, and iodo), oxo, oxa, amino, alkylamino, and dialkyl amino.

Aryl substituents include without limitation phenyl, biphenyl, napthyl, and the like, each being optionally substituted with heteroatoms or functional groups as discussed above. Heterocyclic groups may be aromatic or nonaromatic hydrocarbon rings containing one or more heteroatoms (e.g., N, O, or S) in the ring. Preferred heteroaromatic rings will be either 5-membered or 6-membered ring, each optionally comprising additional heteroatoms or functional groups attached to the ring, as discussed above. Non-limiting examples of five-membered heterocylic rings include, without limitation, pyrrolidine, tetrahydropyran, tetrahydrothiophene, oxazolidine, thiazolidine, 1,3-dioiane, 1,3-oxzthiolane, 1,3-dithiolane, imidazolidine, pyrazolidine, pyrrole, furan, thiophene, oxazole, isoxazole, thiazole, isothiazole, imidazole, pyrazole, 1,3,4-oxadiazole, 1,2,4-oxadiazole, 1,3,4-thiadiazole, 1,2,4-thiadiazole, 1,3,4-triazole, 1,2,3-triazole, and the like. Non-limiting examples of six-membered heterocylic rings include, without limitation, 2H-pyran, tetrahydropyran, piperidine, 1,4-dioxane, morpholine, piperazine, 1,4-dithiane, thiomorpholine, pyridine, pyrazine, pyridazine, pyrimidine, 1,2,3-triazine, 1,2,4-triazine, 1,3,5-triazine, 1,2,3,4-tetrazine, and pentazine, to name a few.

Where it is said that $R_1$ and $R_2$ may be "combinations" of the specified groups (e.g., alkyl, alkenyl, alkynyl, aryl, heteroaryl, etc.), it is meant that substituents comprising two or more of the indicated groups are expressly included, such as for example, alkyl-aryl, aryl-alkyl, and the like.

The five membered ring of formula I has at least one stereocenter, indicated by the asterisk on the carbon atom adjacent to $X_2$, and may have an additional stereocenter in the case where $R_2$ is not hydrogen, also indicated with an asterisk. Each stereocenter may independently be in the R or S configuration. Thus, when $R_2$ is not hydrogen, the compounds of formula I will exist as either the (R,R), (S,S), (R,S), or (S,R) diastereomers, each of which is considered a separate embodiment of the invention, along with mixtures of these stereoisomers. In the case where $R_2$ is hydrogen, the compounds of formula I will be either R or S, each of which is a separate embodiment of the invention, along with racemic mixtures of R and S.

In one embodiment, $X_2$ and $X_3$ each represent $NR^N$, and $X_4$ is oxygen, as represented by the genus of Formula I-a:

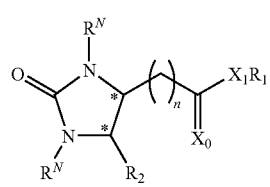

I-a wherein n, $R_1$, $R_2$, $R^N$, $X_0$, and $X_1$ are as defined above. In this embodiment, $R^N$ is preferably, at each occurrence, hydrogen or lower alkyl. In a currently preferred embodiment, $R^N$ is hydrogen at each occurrence, and $R_2$ is lower alkyl, preferably methyl. In a currently preferred embodiment, $X_0$ and $X_1$ each represent oxygen. In another embodiment, $X_0$ is oxygen, sulfur, or $NR^N$, preferably oxygen, and $X_1$ is a group $NR^N$.

In a preferred embodiment, $X_0$, and $X_1$ each represent oxygen and the compound has the structure of Formula I-b:

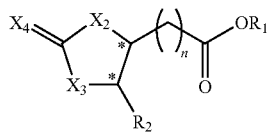

wherein n, $R_2$, $X_2$, $X_3$ and $X_4$ are as defined above. In this embodiment, the compounds are carboxylic acids ($R_1$ is hydrogen) or esters. While $R_1$ is preferably hydrogen, it is also contemplated that esters will be advantageous according to the invention. For example, $R_1$ may be selected to modify the lipophilicity of the compound with higher esters (e.g., $R_1$ is $C_{6-18}$ alkyl) being contemplated to be more lipophilic. Where R1 is hydrogen, it will be understood that the compound can be delivered as a prodrug by selecting an appropriate carboxyl protecting group which is hydrolyzed in vivo to provide the carboxylic acid.

In particular embodiments, according to Formula I-b, $X_4$ is O or S, preferably O; $X_2$ and/or $X_3$ is $NR^N$, most typically NH. In one embodiment, $X_4$ is O, and $X_2$ and $X_3$ are each NH. In certain specific embodiments, $X_2$ and $X_3$ are NH and $X_4$ is O.

In certain embodiments according to Formulas I, I-a, and I-b, "n" is 3, 4, 5, 6, 7, 8, 9 or 10. In each of formulas I, I-a, and I-b it is currently preferred that n is 5.

In each of Formulas I, I-a, and I-b, $R_2$ is most typically a straight chained or branched alkyl, in particular $C_{1-18}$ alkyl, optionally comprising one or more heteroatoms. In specific embodiments, $R_2$ is $C_{1-16}$, $C_{1-14}$, $C_1$-$C_{1-12}$, $C_{1-10}$, $C_{1-8}$, $C_{1-6}$, $C_{1-4}$ or $C_{1-2}$. Typically, $R_2$ will be $C_1$, $C_2$, $C_3$, $C_4$, or $C_5$ alkyl, either straight chained or branched. In certain specific embodiments, $R_2$ is methyl or ethyl.

$R_1$ and $R_2$ are typically (independently) either hydrogen or straight chained or branched alkyl, in particular $C_{1-18}$ alkyl. In specific embodiments, $R_1$ is $C_{1-16}$, $C_{1-15}$, $C_{1-14}$, $C_{1-13}$, $C_{1-12}$, $C_{1-11}$, $C_{1-10}$, $C_{1-9}$, $C_{1-8}$, $C_{1-7}$, $C_{1-6}$, $C_{1-5}$ or less, such as $C_1$, $C_2$, $C_3$, $C_4$, or $C_5$ alkyl, either straight chained or branched. In certain specific embodiments, $R_1$ and/or $R_2$ are methyl or ethyl. In other specific embodiments, $R_1$ and/or $R_2$ are hydrogen.

$R_1$ and $R_2$ may comprise linear alkyl moieties of the form —$(CH_2)_a$—R* where "a" is an integer from 1 to 6, including, for example, —$CH_2$—R*, —$CH_2CH_2$—R*, —$CH_2CH_2CH_2$—R*, or —$CH_2CH_2CH_2CH_2$—R*; linear alkoxy moieties of the general form —$O(CH_2)_a$—R* where "a" is an integer from 1 to 6, including for example, —$OCH_2$—R*, —$OCH_2CH_2$—R*, or —$OCH_2CH_2CH_2$—R*; groups of the form —$O(CH_2)_aO$—R* where "a" is as defined above; —$(CH_2CH_2O)_a$—R* or a moiety of the form —$(CH_2)_bO(CH_2)_c$—R*, —$(CH_2)_bS(CH_2)_c$—R*, or —$(CH_2)_bNR^N(CH_2)_c$—R* wherein "b" and "c" are independently an integer from 0 (zero) to 6 and $R^N$ is as defined above. In each case R* is a lower alkyl (e.g. methyl, ethyl, propyl, butyl, etc.), hydrogen, hydroxyl, thiol, —(CHO), carboxyl, amino, alkylamino, or dialkylamino.

$R_1$ and $R_2$ can also be independently chosen from carbocycles or heterocycles. The carbocycles can be independently saturated, unsaturated or aromatic cycles. The carbon cycles are typically from 3 to 8 carbons, more typically 3 to 7 carbons and most typically from 5 to 6 carbons (e.g., cyclopentyl, or cyclohyexyl), each being optionally substituted. The heterocycles are also independently saturated, unsaturated or aromatic. The heterocycles are typically from 3 to 8 membered rings, more typically 3 to 7 membered rings, and preferably 5 or 6 membered rings. The heterocycles can contain one or more heteroatoms, selected from nitrogen, sulfur or oxygen atoms in the ring.

Currently preferred compounds have the structure according to formula Ic:

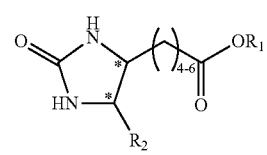

wherein n is from 4 to 6 (preferably 5); $R_2$ is methyl, ethyl, propyl, or butyl, or phenyl (preferably methyl); and R1 is hydrogen, methyl, ethyl, propyl, butyl, pentyl, hexyl, phenyl, or benzyl (preferably hydrogen).

In a particular embodiment, the compound is desthiobiotin which has the structure:

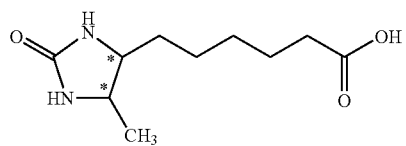

This compound may be present as the (R,R), (R,S), (S,R), or (S,S) stereoisomer, or as a mixture of two or more of these stereoisomers. Formula II includes the compounds L-Desthiobiotin, D-Desthiobiotin, and DL-desthiobiotin. Preferably, the stereocenter to which the methyl group is attached is in the S configuration and the other stereocenter is in the R configuration, as shown below:

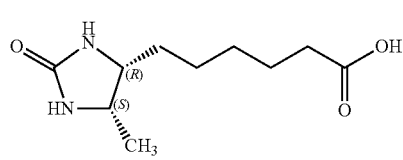

The compound of formula II is D-Desthiobiotin (CAS Registry No. 533-48-2), and is also known as (+)-Dethiobiotin or d-Dethiobiotin.

The compounds described herein can be present in the form of topically acceptable salts or complexes (e.g., non-toxic and/or non-irritating) that retain the biological activity of the compound. The salts may be either inorganic or organic acid or base addition salts. Suitable acid salts include but are not limited to acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfate, glucoheptonate, glycerophosphate, hemisulfate, heptonate, hexanoate, fumarate, hydrochloride, hydrobromide, hydroiodide, 2-hydroxy-ethanesulfate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Special mention may be made of hydrochloride salts. Base addition salts include those formed with metal cations such as zinc, calcium, bismuth, barium, magnesium, manganese, lithium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine, etc. Any nitrogen-containing groups, can be quaternized with lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides such as benzyl and phenethyl bromides, to name a few.

Suitable prodrugs of desthiobiotin and its analogs (e.g., compounds of formula I) include those having the structures of formulas IIIa or IIIb:

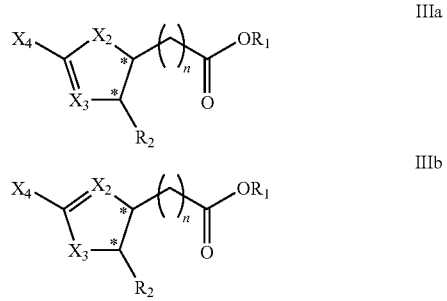

In structure IIIa, $X_3$ is N and $X_4$ is $OR_1$ or $NR^NR_1$; where $R^N$, $R_1$, $R_2$, and $X_2$ are defined as above. In structure IIIb, $X_2$ is N and $X_4$ is $OR_1$ or $NR^NR_1$; where $R^N$, $R_1$, $R_2$, and $X_3$ are defined as above. The prodrugs hydrolyze in vivo to the compounds of formula I.

The topical compositions according to the invention can be formulated in a variety of forms for topical application and will comprise from about 0.0001% by weight to about 10% by weight of the compound. In specific embodiments, the composition comprises from about 0.001% by weight to about 5% by weight, or about 0.01% by weight to about 2.5% by weight of the composition. In certain embodiments, the composition comprises 0.001% to about 1.5% by weight or about 0.01% to about 0.5% by weight of the composition.

The composition may typically formulated as an emulsion (including water-in-oil or oil-in-water emulsions), lotion, cream, serum, spray, aerosol, cake, ointment, essence, gel, paste, patch, pencil, towelette, mask, stick or other forms suitable for topical application.

The compositions can include a cosmetically acceptable vehicle. Such vehicles may take the form of any known in the art suitable for application to skin and may include water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing. In one embodiment, the vehicle comprises liposomes.

The composition may optionally comprise other cosmetic actives and excipients, including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives, stabilizers, pharmaceutical agents, photostabilizing agents, sunscreens, and mixtures thereof. In addition to the foregoing, the cosmetic compositions of the invention may contain any other compound for the treatment of skin disorders.

The composition may comprise additional active ingredients having anti-aging benefits. It may be desirable to include one or more additional LOXL1 enhancers, as it is contemplated that synergistic improvements may be obtained with such combinations. Other suitable antiaging components include, without limitation, certain botanicals, such as *Butea Frondosa* extract, thiodipropionic acid (TDPA), retinoids, alpha-hydroxyacids, and glycolic acid, to name a few.

Methods of treating symptoms of reduced skin elasticity are provided that comprise topically applying effective amounts of any of the compound described herein, or a salt thereof to the skin of an individual in need thereof. Typically, the compounds of the invention are provided in the form of compositions comprising a cosmetically acceptable vehicle, by which is meant a vehicle compatible (e.g., safe) with application to human skin.

The compositions ideally increase LOXL1 activity in the skin. Preferably, the compounds of the present invention have the additional activity of stimulating Fibrillin-1. In certain embodiments, the administration is not to a hair follicle (such as a hair follicle of the scalp). In specific embodiments, the host is not suffering from an increase in sebum production. In certain embodiments, the skin is not suffering from an increase in sebum production. The skin damage that can be improved or treated with the compounds of the invention include any signs of reduced skin elasticity such as fine lines and/or wrinkles, fragile or thinning skin, sagging skin, lackluster skin, fatigued skin, dry skin, skin sensitivity, dark eye circles, puffy skin, irregular skin pigmentation, and melasma.

Topically applying compositions of the present invention to the skin can enhance and improve the aesthetic appearance of skin. This method is particularly useful for treating signs of skin photo- and intrinsic ageing, including fine lines and wrinkles, skin tone and coloration, skin sagging and atrophy, enlarged pores, skin thinning, decreased resilience and turgor.

The invention also provides a method for treating aging skin by topically applying a composition comprising the inventive composition over the affected area for a period of time sufficient to reduce, ameliorate, dermatological signs of reduced skin elasticity. The composition will typically be applied to the skin from 1 to 3 times per 24 hours for as long as is necessary to achieve desired results. The treatment regiment may comprise daily application for at least one week, at least two weeks, at least four weeks, at least eight weeks, or at least twelve weeks. The method includes treatment of skin changes associated with both chronological and intrinsic skin aging. The method is contemplated to be particularly useful for the treatment of UV damaged skin.

In one embodiment, a method of treating wrinkles of the skin (e.g., on the face, neck, hands) comprises topically applying a cosmetic composition comprising desthiobiotin or a salt and/or ester thereof to the wrinkle in an effective amount and for a time sufficient to reduce the severity or depth of the wrinkle.

In another embodiment, a method of treating sagging of the skin (e.g., on the face or neck) comprises topically applying a cosmetic composition comprising desthiobiotin or a salt and/or ester thereof to the sagging skin in an effective amount and for a time sufficient to reduce the degree of sagging.

In another embodiment, a method of treating thin skin comprises topically applying a cosmetic composition comprising desthiobiotin or a salt and/or ester thereof to an thin skin in an effective amount and for a time sufficient to reduce the degree of sagging.

In another embodiment, a method of treating enlarged pores comprises topically applying a cosmetic composition comprising desthiobiotin or a salt and/or ester thereof to an enlarged pore in an effective amount and for a time sufficient to reduce the degree of sagging.

1. EXAMPLES 1.1 Example 1

Stimulation of LOXL1 Activity by DL-Desthiobiotin

The enzyme lysyl oxidase-like 1 ("LOXL1"), has been found to be a key regulator of the renewal of elastin polymer, an extracellular matrix component providing connective tissues, including the skin, with elastic properties. Elastin is not believed to be produced past puberty, after which maintenance of the elastin fiber is the result of competing antielastase-elastase activities. As age progresses, an imbalance in the competing activities is noted, resulting in a loss of elasticity in elastin containing tissues. With respect to skin, this loss of elasticity is most commonly observed as wrinkles.

Although the exact mechanisms of renewal/degradation (i.e., antielastase/elastase activity) are unknown, LOXL1 has been identified as an "antielastase" factor, mediating the renewal of elastin fibers by polymerization of tropoelastin monomers (see, e.g., Kagan et al., 2003, *J. Cell. Biochem.* 88:660-672; and Li et al., 2004, *Nat. Genet.* 36:178-182, each of which is hereby incorporated by reference in its entirety). Accordingly, agents that act to increase LOXL1 transcription and/or translation or LOXL1 activity will increase "antielastase" activity, fostering renewal of elastin fibers and effecting an improvement in elasticity of elastin containing tissues. The ability of DL-Desthiobiotin to induce expression of LOXL1 was assayed using a luciferase-reporter system. Addition of DL-Desthiobiotin to cultures comprising LOXL1 regulatory elements was found to induce expression of reporter genes significantly over that of controls.

1.1.1 Materials and Methods

Vector construction, transfection and expression: The promoter region of the LOXL1 gene was isolated and cloned into the pGL3 Luciferase reporter plasmid (Promega) by standard methods known in the art and according to manufacturer's instructions. The LOXL1/pGL3 vector and the control vector pRL-NULL (Promega), containing no regulatory elements, were contransfected into the human fibrosarcoma line HTI080 using LipofectAMINE™ LTX Reagent (Invitrogen) according to manufacturer's directions.

Transfected cells were allowed to recover for 24 h. The culture medium was then replaced with fresh medium containing various concentrations of DL-Desthiobiotin, and the transfected cells cultured for an additional 24 h.

The cultures were subsequently washed with PBS and exposed to 100 microlit cell lysis buffer/25 $cm^2$ culture area and gently shaken at room temperature for 30 min. The culture flasks containing the cell lysate were then immediately placed at −80° C.

Determination of reporter activity: The activity of the reporter gene, firefly luciferase, was determined according to the manufacturer's instructions (Dual-Luciferase® Reporter Assay System, Promega). Briefly, the activity of the reporter gene is determined relative to that of a control vector encoding a second luciferase gene, that from *Renilla reniformis*. The relative activities of the genes from test and control cultures are compared for a determination of percent modification of regulatory sequence activity.

1.1.2 Results

Because pGL3 vectors lack the necessary promoter regions to regulate the luciferase gene, the expression of this gene is controlled by the cloned regulatory elements, in this case the regulatory elements of the LOXL1 gene. In triplicate tests, the addition of 0.001% of DL-Desthiobiotin was found to increase expression of the reporter gene by 90% ($p<0.05$, compared to vehicle control). DL-Desthiobiotin is thus indicated as a positive regulator LOXL1 expression, suggesting secondary effects on elastin renewal.

1.2. Example 2

Stimulation of Fibrillin-1 by DL-Desthiobiotin

Fibrillin-1 is a 340 kDa protein that is a constituent of microfibrils in skin Fibrillin microfibrils are widely distributed microfibrils and they confer long range elasticity to connective tissue. They direct tropoelastin deposition during elastic fibrillogenesis and form an outer mantle for mature elastic fibers. Mutations in fibrillin-1 cause Marfan syndrome, a heritable disease associated with severe aortic, ocular and other abnormalities due to defective elastic fibers (Kielty et al, *Adv. in Protein Chemistry*, vol 70, p. 405, 2004). Agents that increase fibrillin-1 expression will further increase "antielastase" activity, fostering renewal of elastin fibers and effecting an improvement in elasticity of elastin containing tissues. The ability of DL-Desthiobiotin to induce expression of fibrillin-1 was assayed by quantitative RT-PCR. Addition of DL-Desthiobiotin to human fibroblast cell cultures was found to induce expression of fibrillin-1 mRNA significantly over that of controls.

1.2.1 Materials and Methods

Cell Treatment: Normal human dermal fibroblasts were plated at $10^6$ cells/100 mm tissue culture plates in 10 mls of standard growth medium and incubated at 37° C. and 10% $CO_2$.

Approximately 24 hours later, cells were dosed with test actives and solvent controls diluted in fresh growth medium and incubated for 48 hours at 37° C. Following 48-hour incubation, cell medium was removed, and 1 ml of TRIzol® reagent was added to lyse the cells in each plate. Cells from each plate were scraped, passed several times through a pipette, and collected into 1.5 ml centrifuge tubes. The cell lysates were incubated for 5 minutes at 15 to 30° C. to permit the complete dissociation of nucleoprotein complexes, and then stored at −80° C. for RNA isolation.

RNA Isolation and RT PCR: RNA was isolated using standard procedures and was dissolved in RNase-free water and stored at −80° C. The concentration of total RNA was determined by using Agilent 2100 Bioanalyzer. RNA 6000 Nanochip revealed that RNA sample was intact.

Reverse Transcriptase (RT) reactions were conducted following the manufacturer's instructions provided by Applied Biosystems, Calif. After the RT step, the reactions were stored at −20° C. for QPCR analysis. QPCR was conducted in a total volume of 20 μl. Applied Biosystems (AB) Universal PCR master mix was used. The mixture was prepared to contain 10 μl of Taqman Universal PCR mix, 1 μl of primer and probe mix, 2 μl of RT product, and 7 μl of deionized water. Both Fibrillin-1 and GAPDH primers and probes were purchased from Applied Biosystems, and ID for Fibrillin-1 is Hs00171191_m1, and human GAPDH is 4352934E. The temperature profiles for QPCR were 50° C. for 2 min, and 95° C. for 10 min for 1 cycle, then at 95° C. for 15 sec, and 60° C. for 1 min for 40 cycles.

1.2.2 Results

Results: QPCR results showed that treatment with 0.001% DL-Desthiobiotin increased Fibrillin-1 gene expression by 47.55% compared to solvent control (p<0.05).

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method of treating one or more signs of skin aging associated with a loss of elastin comprising topically applying to the skin a composition effective in treating said one or more signs of skin aging associated with loss of elastin, said composition comprising:

(i) an effective amount of a compound of Formula I:

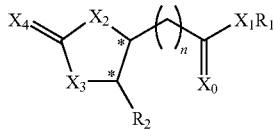

wherein:
n is an integer from 3 to 12;
$X_0$ and $X_4$ are each O;
$X_1$ is selected from the group consisting of O, S, and $NR^N$, where $R^N$ represents hydrogen, lower alkyl, $COR_3$, $CO_2R_3$, or $CH(OR_3)_2$; wherein $R_3$ in each case is independently selected from the group consisting of H, alkyl, alkenyl, alkynyl, aryl, alkylaryl;
$X_2$ and $X_3$ are each $NR^N$, where $R^N$ represents hydrogen, lower alkyl, $COR_3$, $CO_2R_3$, or $CH(OR_3)_2$; wherein $R_3$ in each case is independently selected from the group consisting of H, alkyl, alkenyl, alkynyl, aryl, alkylaryl, and heteroaryl;
$R_1$ is selected from the group consisting of H, alkyl, cycloalkyl, alkenyl, alkynyl, aryl, heteroaryl, alkylaryl, alkoxyalkyl, and carboxyamidoalkyl; and $R_2$ is selected from the group consisting of H, alkyl, alkenyl, alkynyl, aryl, alkylaryl, heteroaryl, alkoxy, aryloxy, and thioalkoxy;
or a topically acceptable salt or prodrug thereof; and
(ii) a cosmetically acceptable vehicle.

2. The method according to claim 1 wherein n is an integer from 4 to 6.

3. The method according to claim 1 wherein n is 5.

4. The method according to claim 1 wherein $R_2$ is $C_{1-5}$ alkyl.

5. The method according to claim 4 wherein $R_2$ is methyl.

6. The method according to claim 1 wherein $X_2$ and $X_3$ are NH.

7. The method according to claim 6 wherein $X_1$ is O.

8. The method according to claim 7 wherein $R_1$ is H.

9. The method according to claim 7 wherein $R_1$ is $C_{1-6}$ alkyl.

10. The method according to claim 1 wherein said compound is desthiobiotin.

11. The method according to claim 10 wherein said compound is D-desthiobiotin.

12. The method according to claim 1 wherein said one or more signs of skin aging includes wrinkles and/or fine lines.

13. The method according to claim 1 wherein said one or more signs of skin aging includes skin sagging or atrophy.

14. The method according to claim 1 wherein said one or more signs of skin aging includes thin skin.

15. The method according to claim 1 wherein said one or more signs of skin aging includes enlarged pores.

16. The method according to claim 1 wherein said one or more signs of skin aging includes loss of skin tone or coloration.

17. The method according to claim 1 wherein the composition comprises from about 0.001% by weight to about 5% by weight of the compound or salt or prodrug thereof.

18. A method for treating one or more signs of skin aging associated with a loss of elastin comprising topically applying to skin in need thereof, a cosmetic composition effective in treating said one or more signs of skin aging associated with loss of elastin, said composition comprising, in a cosmetically acceptable vehicle, an effective amount of a compound having the structure:

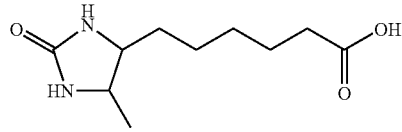

or a salt or ester thereof; wherein said one or more signs of skin aging are selected from the group consisting of fine lines or wrinkles, skin sagging or atrophy, thin skin, enlarged pores, and decreased skin resilience or turgor, and combinations thereof.

19. The method according to claim 18, wherein said compound is D-Desthiobiotin or a salt or ester thereof.

20. The method according to claim 19, wherein said one or more signs of skin aging is wrinkles or fine lines.

21. The method according to claim 1, wherein said compound that is topically applied to the skin is a prodrug of the compound of formula I.

22. The method according to claim 1, wherein $R^N$ is H or $C_{1-6}$ alkyl.

23. The method according to claim 1, wherein the compound or salt or prodrug thereof is present in an amount effective to enhance lysyl oxidase-like 1 (LOXL1) activity, thereby treating said one or more signs of skin aging associated with loss of elastin.

24. The method according to claim 1, wherein the compound or salt or prodrug thereof is present in an amount effective to enhance Fibrillin-1 activity, thereby treating said one or more signs of skin aging associated with loss of elastin.

25. The method according to claim 18, wherein the compound or salt or ester thereof is present in an amount effective to enhance lysyl oxidase-like 1 (LOXL1) activity, thereby treating said one or more signs of skin aging associated with loss of elastin.

26. The method according to claim 18, wherein the compound or salt or ester thereof is present in an amount effective to enhance Fibrillin-1 activity, thereby treating said one or more signs of skin aging associated with loss of elastin.

27. A method of treating one or more signs of skin aging associated with a loss of elastin comprising topically applying to the skin a composition effective in treating said one or more signs of skin aging associated with loss of elastin, said composition comprising:

(i) an effective amount of a compound of Formula I:

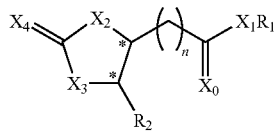

wherein:
n is an integer from 4 to 6;
$X_0$ and $X_4$ are each O;
$X_1$ is selected from the group consisting of O, S, and $NR^N$, where $R^N$ is hydrogen or lower alkyl;
$X_2$ and $X_3$ are each $NR^N$, where $R^N$ is hydrogen or lower alkyl;
$R_1$ is selected from the group consisting of H, alkyl, alkenyl, and alkynyl; and
$R_2$ is selected from the group consisting of H, alkyl, alkenyl, and alkynyl;
or a topically acceptable salt or prodrug thereof; and
(ii) a cosmetically acceptable vehicle.

\* \* \* \* \*